(12) United States Patent
Luo et al.

(10) Patent No.: US 10,375,937 B2
(45) Date of Patent: Aug. 13, 2019

(54) BREEDING METHOD FOR OBTAINING HETEROSIS IN LINED SEAHORSES

(71) Applicant: SOUTH CHINA SEA INSTITUTE OF OCEANOLOGY, Guangdong (CN)

(72) Inventors: Wei Luo, Guangdong (CN); Qiang Lin, Guangdong (CN); Geng Qin, Guangdong (CN); Xin Wang, Guangdong (CN); Yanhong Zhang, Guangdong (CN); Huixian Zhang, Guangdong (CN)

(73) Assignee: SOUTH CHINA SEA INSTITUTE OF OCEANOLOGY, Guangdong (CN)

( * ) Notice: Subject to any disclaimer, the term of this patent is extended or adjusted under 35 U.S.C. 154(b) by 237 days.

(21) Appl. No.: 15/325,720

(22) PCT Filed: Dec. 4, 2015

(86) PCT No.: PCT/CN2015/096490
§ 371 (c)(1),
(2) Date: Jan. 12, 2017

(87) PCT Pub. No.: WO2017/004936
PCT Pub. Date: Jan. 12, 2017

(65) Prior Publication Data
US 2017/0142941 A1 May 25, 2017

(30) Foreign Application Priority Data
Jul. 9, 2015 (CN) .......................... 2015 1 0399711

(51) Int. Cl.
*A01K 61/00* (2017.01)
*A01K 67/027* (2006.01)
(Continued)

(52) U.S. Cl.
CPC ............ *A01K 67/027* (2013.01); *A01K 61/10* (2017.01); *A01K 61/95* (2017.01); *A01K 67/02* (2013.01); *Y02A 40/812* (2018.01)

(58) Field of Classification Search
CPC ...... A01K 67/027; A01K 61/00; A01K 61/10; A01K 61/95; A01K 67/02; A01K 2227/40
See application file for complete search history.

(56) References Cited

U.S. PATENT DOCUMENTS

2012/0304322 A1* 11/2012 Yamaha ............... A01K 67/027
800/20
2014/0331346 A1* 11/2014 Hu ...................... C12N 15/8509
800/22

(Continued)

OTHER PUBLICATIONS

Chang et al., "Hybridization effects of the different geographic population of Chlamys f arreri," Acta Oceanologica Sinica, Mar. 2006, pp. 114-120.

(Continued)

*Primary Examiner* — Trinh T Nguyen
(74) *Attorney, Agent, or Firm* — JCIPRNET

(57) ABSTRACT

The present invention discloses a breeding method for obtaining heterosis in lined seahorses, which comprises the following steps: S1, selecting parents of lined seahorse from populations with great differences in genetic background; S2, intensified rearing the parents before pregnancy; S3, matching and breeding the parents of lined seahorse from different geographical populations according to complete diallel cross method; S4, finely nursing pregnant seahorses; S5, respectively collecting all postlarvae (filial generations) hatched by each breeding group in one week; S6, rearing the filial generations; and S7, comparing survival rate and growth performance of filial generations. The present invention, via hybridization of different geographical populations to obtain lined seahorse, makes effective use of heterosis.

(Continued)

Survival rate and growth rate of filial generations are apparently enhanced compared to that of those filial generations without hybridization. Such method enhances genetic diversity of lined seahorses and accelerates breeding of fine strain of lined seahorses.

10 Claims, 1 Drawing Sheet

(51) Int. Cl.
    *A01K 61/95*     (2017.01)
    *A01K 61/10*     (2017.01)
    *A01K 67/02*     (2006.01)

(56) References Cited

U.S. PATENT DOCUMENTS

2016/0309685 A1* 10/2016 Lightner ............... A01K 67/02
2017/0105392 A1* 4/2017 Lin ....................... A01K 61/10

OTHER PUBLICATIONS

Bierne et al., "Microsatellite-associated heterosis in hatchery-propagated stocks of the shrimp *Penaeus stylirostris*," Aquaculture, Apr. 2000, pp. 203-219.
Bryden et al., "Performance and heterosis in farmed and wild Chinook salmon (*Oncorhynchus tshawytscha*) hybrid and purebred crosses," Aquaculture, Jun. 2004, pp. 249-261.
Wang et al., "Prediction of hybridization advantage among five strains of rainbow trout by combination ability and SSR markers," Journal of Fishery Sciences of China, Mar. 2009, pp. 206-213.

\* cited by examiner

BREEDING METHOD FOR OBTAINING HETEROSIS IN LINED SEAHORSES

CROSS-REFERENCE TO RELATED APPLICATION

This application is a 371 application of International PCT application serial no. PCT/CN2015/096490, filed on Dec. 4, 2015, which claims the priority benefit of Chinese application no. 201510399711.5, filed on Jul. 9, 2015. The entirety of each of the abovementioned patent applications is hereby incorporated by reference herein and made a part of this specification.

TECHNICAL FIELD

The present invention relates to the technical field of fish crossbreeding, and more specifically, relates to a breeding method for obtaining heterosis by intraspecific hybridization of lined seahorses from different populations.

BACKGROUND OF THE PRESENT INVENTION

Seahorse, belonging to *pisces*, syngnathidae, *hippocampus*, as a precious marine traditional Chinese medical material, known as "southern ginseng" in China, is provided with effects such as invigorating kidney, strengthening Yang, strengthening heart, hastening parturition, hemostasis, analgesic, tranquilizing and allaying excitement. Lined seahorse (*Hippocampus Erectus*), mainly located at the west coast of the Atlantic, is a typical tropic and subtropic type of seahorse population with strong fertility, large size and fast growth rate. In recent years, lined seahorse has been introduced from United States to China by multiple Chinese companies, and it has been bred in coastal areas such as Hainan, Guangdong, Fujian and Shandong. So far, lined seahorse has become one of the main aquaculture species in China. However, after several generations of propagation, degeneration of germplasm in lined seahorse is very severe. The inventor team of the present invention had done researches on the current situation of aquaculture in partial coastal areas of China during 2010~2014 continuously. They found that the propagation and aquaculture pattern of seahorses in China extremely lagged behind. Inbreeding depression was so severe that the quantity of spawning from parental generation decreased by 30~60% compared to that from primary generation, while survival rate of larva was only 15~25% and growth rate of young seahorse decreased by approximately 30% compared to that of primary generation. Thus, at the present stage, germplasm of lined seahorse has depressed obviously and quality of larva has become one of the "bottlenecks" restricting the development of seahorse aquaculture in China.

Heterosis is a common biological phenomenon, which means a phenomenon that two parents with different genetic backgrounds hybridize with each other to generate a hybrid F1 generation with improvements in aspects such as vitality, adaptability, stress resistance and productivity as compared to the purebred. Crossbreeding is currently one of the most widely used and most successful methods for genetic improvement of animals and plants at home and abroad. In the field of aquaculture, crossbreeding is also one of the main routes for improving the present situation of aquaculture. Nowadays, crossbreeding of several aquatic animals such as *Chlamys Farreri* (Chang et al. 2006), *Penaeus Stylirostris* (Bierne et al. 2000), *Oncorhynchus Tshawytscha* (Bryden et al. 2004), *O. Mykiss* (Wang et al. 2009) and so forth has tremendously progressed. However, by far, there still hasn't been any international research or report about crossbreeding of lined seahorse.

SUMMARY OF THE PRESENT INVENTION

The technical problem to be solved by present invention is to overcome the deficiencies of depression in germplasm of lined seahorse and quality reduction of larva currently encountered, and to provide a method for obtaining heterosis by hybridization among different geographical populations from multiple cultured populations of lined seahorse in China. Thus the lined seahorse with high survival rate and fast growth rate can be obtained for improving the present situation whereby the aquaculture of seahorse lacks fine variety.

An object of the present invention is to provide a breeding method for obtaining heterosis in lined seahorses.

The above-mentioned object of the present invention can be realized by following technical solutions:

A breeding method for obtaining heterosis in lined seahorses comprises following steps:

S1, selecting parents of lined seahorse from populations with great differences in genetic background;

S2, intensified rearing the parents of lined seahorse in S1;

S3, completely diallel crossing, matching and breeding the parents of lined seahorse from different populations in S2 according to provenance;

S4, finely nursing pregnant parents of each breeding group obtained in S3 to avoid abortion;

S5, respectively collecting all filial generations hatched by the pregnant parents of each breeding group in S4 in one week;

S6, finely nursing the filial generations in S5 according to a same feeding mode in a similar environment;

S7, by comparison of survival rate and growth performance of the filial generations, obtaining fine strain of lined seahorses with high survival rate, fast growth rate and good genetic diversity.

According to survey, lined seahorses from different cultured populations in areas such as Shenzhen Guangdong, Dongshan Fujian and Yantai Shandong, which were introduced from United States after 2009, have large differences in genetic background.

Thus, preferably, in S1, aquaculture populations of Shenzhen Guangdong, Dongshan Fujian and Yantai Shandong are selected as parents. The lined seahorses which are energetic, disease-free, harmless, healthy and strong, with well-developed gonads, are selected as parents for breeding and pairing. Preferably, ages of the parents are all 1~1.5 years old, weights of male parents are over 10.0 g and weights of female parents are over 8.0 g, and differences of weights between all male parents or female parents are less than or equal to 2.0 g.

Preferably, methods for intensified rearing mentioned in S2 are as follows: in 1~2 month after seahorse parents have been introduced, males and females are separated for feeding and are reared alone for a half month. During this period, water temperature is maintained between 22~30° C. The parents are under intensified rearing by being mainly fed with frozen shrimps and accompanied by copepods as well as artemia nauplii as baits. Daily feeding amount of the frozen shrimps is 5%~8% of total weight of the lined seahorses, and there are three feedings every day which are at 8 a.m., 1 p.m. and 6 p.m. respectively.

More preferably, the seahorse parents are put into a white bucket for intensified rearing. Artificial aquatic plants are provided inside the white bucket for the seahorses to rest.

Preferably, specific methods for completely diallel crossing the parents according to the provenance mentioned in S3 are as follows:

S31, performing matching in accordance with nine groups: Yantai♀×Yantai♂, Yantai♀×Shenzhen♂, Yantai♀×Dongshan♂, Shenzhen♀×Shenzhen♂, Shenzhen♀×Yantai♂, Shenzhen♀×Dongshan♂, Dongshan♀×Dongshan♂, Dongshan♀×Yantai♂ and Dongshan♀×Shenzhen♂;

S32, respectively putting parents of each group in S31 into imitating ecotype white buckets for matching and breeding; each imitating ecotype white bucket contains 4 pairs or more than 4 pairs of parents; and each breeding group comprises 12 pairs or more than 12 pairs of parents.

More preferably, each imitating ecotype white bucket mentioned in S32 contains same amount of female and male parents respectively. During operation, make sure the seahorses are handled gently and put latex gloves on. Seahorses twining together are separated gently under water in order to reduce the stimulation and harm to seahorses as much as possible (seahorses may be under reproductive disturbance or abortion when they are stimulated at this moment, and epidermal injury may easily cause infection of pathogenic bacterium on seahorses which will enhance the risk of disease). After the parents are put into the white buckets, stimulation of slight water flow in 0.05 $m^3$/h is maintained. A quiet environment is guaranteed every morning (seahorses mostly mate at morning and providing the quiet environment can prevent generating disturbance to the seahorses).

At this moment, male and female parents are first in heat, move in parallel and chase each other. When reaching climax, a brood pouch of the male begins to bulge and a pouch opening opens, while a genital of the female extrudes; when tails of male and female twine together, an ovum is ovulated by the female into the brood pouch of the male, and the fertilization is completed.

Preferably, specific conditions of fine nursing mentioned in S4 are as follows: a quiet environment of aquaculture is maintained and temperature difference of water is no more than 3° C.; operation should be fast and gentle during artificial inspection on physical condition of the seahorse, also the seahorses should not be kept out of water for more than 2 minutes; daily feeding amount during pregnancy should be reduced compared to the period without pregnancy, and the seahorses are fed with frozen shrimps 3~5 times daily while the total feeding amount is 4%~7% of the weight of seahorse.

Preferably, fine nursing mentioned in S6 is in similar conditions and same management ways. The filial generations of different breeding groups are put into buckets (preferably, the volume of said bucket is 1 $m^3$) separately for rearing, and density is 500 seahorses/$m^3$. The seahorses are fed with artemia nauplii as baits mainly, and the suitable feeding amount of baits is whereby a little bit of the baits are left in water when the seahorses are fed again. When the seahorses are 1 month old, they are transferred to a small size concrete pond (preferably, the volume of said small size concrete pond is 9 $m^3$) for rearing, and density is 100 seahorses/$m^3$. The seahorses are fed with artemia nauplii and frozen shrimps while daily feeding amount of frozen shrimps is 5%~8% of total weight of seahorses. When the seahorses are 2~3 months old, they are transferred to an adult fish rearing pond (preferably, the volume of said adult fish rearing pond is 16 $m^3$) for rearing, and density is 20 seahorses/$m^3$. The seahorses are fed with frozen shrimps while daily feeding amount of frozen shrimps is 5%~8% of total weight of seahorses.

Preferably, specific methods for comparison of survival rate and growth performance of the filial generations mentioned in S7 are as follows: the survival rates of the filial generations from each breeding group are compared when the seahorses are 1, 2 and 4 months old respectively. When the seahorses are 4 months old (a period that the lined seahorses become marketable fish), weights of lined seahorses from each group are compared.

As a preferable implementation, specific operation procedures of above-mentioned breeding method for obtaining heterosis in lined seahorses are summarized herein below:

(1) Selecting parents of lined seahorses from populations with great differences in genetic background;

Parents collected in this step are from cultured populations of Shenzhen Guangdong, Dongshan Fujian and Yantai Shandong (according to survey, lined seahorses from different geographical populations in areas such as Shenzhen Guangdong, Dongshan Fujian and Yantai Shandong, which were introduced from United States after 2009, have large differences in genetic background.).

The lined seahorses which are energetic, disease-free, harmless and strong, with well-developed gonads, are selected as parents. The quantity of parents introduced from each population is over 80 pairs. Ages of the parents are all 1~1.5 years old, weights of male parents are over 10.0 g and weights of female parent are over 8.0 g, and differences of weights between all male parents or female parents are less than or equal to 2.0 g.

(2) Intensified rearing parents of lined seahorse;

In 1~2 month after seahorse parents have been introduced, they are under intensified rearing before pregnancy. The water temperature is maintained between 22~30° C. The parents are fed with artemia nauplii and frozen shrimps as baits. There are three feedings every day which are at 8 a.m., 1 p.m. and 6 p.m. respectively. Daily feeding amount of frozen shrimps is 5%~8% of total weight of the lined seahorses.

(3) Matching and breeding the parents of lined seahorse from different populations according to a method of complete diallel cross;

Male and female parents are put into imitating ecotype white buckets for complete diallel cross according to provenance, that is nine groups of Yantai♀×Yantai♂, Yantai♀×Shenzhen♂, Yantai♀×Dongshan♂, Shenzhen♀×Shenzhen♂, Shenzhen♀×Yantai♂, Shenzhen♀×Dongshan♂, Dongshan♀×Dongshan♂, Dongshan♀×Yantai♂ and Dongshan♀×Shenzhen♂ and etc.

Each bucket respectively contains 4 female and 4 male parents selected from candidates randomly, and there are 3 parallels for each group. During the operation, make sure the seahorses are handled gently and put latex gloves on. Seahorses twining together are separated gently under water in order to reduce the stimulation and harm to the seahorses as much as possible. Seahorses may be under reproductive disturbance or abortion when they are stimulated at this moment, and epidermal injury may easily cause infection of pathogenic bacterium on seahorses which will enhance the risk of disease.

After the parents are put into the white buckets, stimulation of slight water flow in 0.05 $m^3$/h is maintained. The seahorses mostly mate at morning. By this time, providing a quiet environment can prevent generating disturbance to the seahorses.

After staying in the white bucket for 2~7 days, male and female parents are first in heat, move in parallel and chase each other. When reaching climax, a brood pouch of the male begins to bulge and a pouch opening opens, while a genital of the female extrudes. When tails of male and female twine together, an ovum is ovulated by the female into the brood pouch of the male, and the fertilization is completed.

(4) Rearing and nursing of pregnant seahorses

During pregnancy, male seahorses are weak and sensitive to external disturbance, so they need fine nursing. Thus, the environment of aquaculture should be kept quiet and temperature difference of water is no more than 3° C.; operation should be fast and gentle during artificial inspection on physical condition of the seahorse, also the seahorses should not be kept out of water for more than 2 minutes. Daily feeding amount during pregnancy should be reduced compared to the period without pregnancy, and the seahorses are fed with frozen shrimps 3~5 times daily while the total feeding amount is 4%~7% of the weight of seahorse. The male discharges the fertilized eggs after the fertilized eggs grew in the brood pouch for 15~22 days.

(5) Respectively collecting all postlarvae hatched by each breeding group in one week;

Time of fertilization and pregnancy of seahorses vary, thus, time of spawn of parents varies too. In order to avoid greater errors made by the differences in time of birth, all of the postlarvae hatched by each breeding group within one week are collected only.

(6) Rearing the filial generations in same feeding mode and similar conditions;

All filial generations are under rearing in same management way and similar conditions. Postlarvae newly hatched are collected into buckets (the volume is 1 m$^3$) for rearing, and density is 500 seahorses/m$^3$. The seahorses are fed with artemia nauplii as baits mainly and the suitable feeding amount of baits is whereby a little bit of the baits are left in water when the seahorses are fed again. When the seahorses are 1 month old, they are transferred to a small size concrete pond (the volume is 9 m$^3$) for rearing, and density is 100 seahorses/m$^3$. The seahorses are fed with artemia nauplii and frozen shrimps while daily feeding amount of frozen shrimps is 5%~8% of total weight of seahorses. When the seahorses are 2~3 months old, they are transferred to an adult fish rearing pond (the volume is 16 m$^3$) for rearing, and density is 20 seahorses/m$^3$. The seahorses are fed with frozen shrimps while daily feeding amount is 5%~8% of total weight of seahorses.

(7) Comparison of growth performance and survival rate of filial generation of seahorse.

When the seahorses are 1, 2 and 4 months old respectively, quantity of the filial generations from each breeding group is calculated and survival rates thereof are compared; when the seahorses are 4 months old (a period that lined seahorse become marketable fish), filial generations from each group are weighed and weights of each group are compared.

As we all know, crossbreeding relates to different geographical populations (genetic background is relatively large), and factors like life habit or suitable life environment thereof vary subtly. Thus whether the hybridization of different populations is successfully completed, whether filial generations after hybridization can normally grow, and survival rates of the filial generations, are influenced by several factors such as biological characteristics of seahorse, artificial operation skill and environment of aquaculture. The crossbreeding method of lined seahorses in present invention can be obtained by abundant researches and explorations, and crossbreeding of lined seahorses from different geographical populations (genetic background is relatively large) can be performed successfully and efficiently. By heterosis via the breeding method in present invention, survival rate and growth rate of the lined seahorse are obviously enhanced, genetic diversity of aquaculture populations is enhanced, germplasm of lined seahorse larva is enhanced, and breeding of fine strain is accelerated.

The present invention has following beneficial effects:

(1) The present invention covers the blank of crossbreeding technology of lined seahorses in the prior art and provides a breeding method for obtaining heterosis in lined seahorses. By such method, the lined seahorse with high survival rate and fast growth performance is reared. It can solve the problem of depression in germplasm of lined seahorses as well as quality reduction of larva, and improves the present situation whereby the aquaculture of seahorse lacks fine variety.

(2) The present invention makes effective use of heterosis via the method, can accelerate breeding of fine strain of lined seahorse and can enhance genetic diversity of lined seahorse.

(3) The present invention obtains apparent heterosis in survival rate and growth rate by hybridization of different geographical populations with apparent diversity in which filial generations of lined seahorses present transgressive phenomena in several important economic characters.

DETAILED DESCRIPTION OF THE PREFERRED EMBODIMENT

Figure 1:
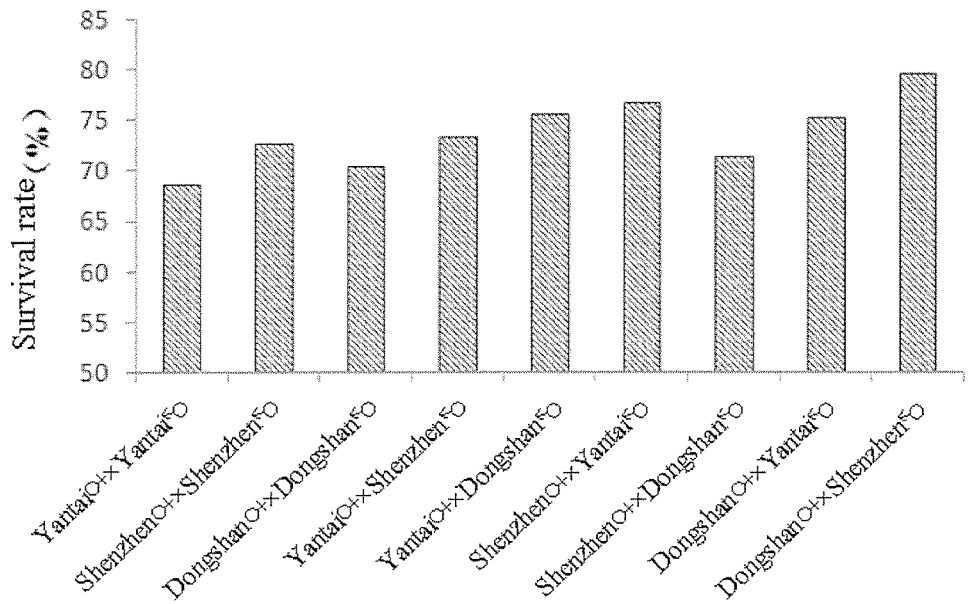
FIG. 1 shows the schematic drawing of survival rate of diallel cross filial generations from lined seahorse populations of Shenzhen, Dongshan and Shandong.

The present invention will be further described below in combination with accompanied drawings of description and specific embodiments which are not intended to limit the invention in any manner. Unless otherwise specified, reagents, methods and equipments used in the present invention are routinely used reagents, methods and equipments in this field of art.

Unless otherwise specified, all reagents and materials used in following embodiments are commercially available.

Embodiment 1

A breeding method for obtaining heterosis in lined seahorses, steps of which are as follows:

1. Introducing lined seahorses from different geographical populations as parents and intensified rearing is performed before pregnancy.

(1) Introducing Parents

According to survey, the lined seahorses from different geographical populations in areas such as Shenzhen Guangdong, Dongshan Fujian and Yantai Shandong, which were introduced from United States after 2009, have greater differences in genetic background.

In February 2013, 80 pairs, 82 pairs and 85 pairs of lined seahorse parents were introduced from cultivation companies of lined seahorse in Shenzhen Guangdong, Dongshan Fujian and Yantai Shandong respectively, and they were raised in Zhanjiang Guangdong.

(2) Selecting Parents

Ages of introduced parents were 1~1.5 years old, weights of female seahorse parents were at least 8.0 g, weights of male seahorse parents were at least 10.0 g, and differences of weights between parents were no more than 2.0 g. Lined seahorses which were energetic, disease-free, harmless and strong, with well-developed gonad, were selected as the parents.

(3) Intensified Rearing of Parents Before Pregnancy

In 1~2 month after seahorse parents were introduced, they were put into a white bucket for rearing. Artificial aquatic plants were provided inside the white bucket for the seahorses to rest. During rearing of the parents, water temperature was maintained between 22~30° C. The parents were fed with frozen shrimps mainly accompanied by copepods and artemia nauplii as baits. Daily feeding amount of frozen shrimps was 5%~8% of weight of lined seahorse and there were three feedings every day which were at 8 a.m., 1 p.m. and 6 p.m. respectively. This batch of lined seahorses was intended to be the basic populations for strain breeding of seahorses with high survival rate and fast growth rate.

2. Matching and breeding of parents according to complete diallel cross (1) On Mar. 20, 2013, seahorse parents were introduced under intensified rearing for 1 month, the growth was normal and the brood pouches and gonads were well-developed. Female and male seahorses (four for each gender) which were energetic and without injury on body surface were selected randomly from each population and put into the white buckets. They were matched by the method of complete diallel cross when put into the white buckets, that is Yantai♀×Yantai♂, Yantai♀×Shenzhen♂, Yantai♀×Dongshan♂, Shenzhen♀×Shenzhen♂, Shenzhen♀×Yantai♂, Shenzhen♀×Dongshan♂, Dongshan♀×Dongshan♂, Dongshan♀×Yantai♂ and Dongshan♀×Shenzhen♂. Three parallel experiments are set for each group, that is, there were 12 pairs of seahorse parents for each breeding group.

(2) Parents for each breeding group were put into imitating ecotype white buckets. During operation, make sure the seahorses are handled gently and put latex gloves on. Seahorses twining together were separated gently under water in order to reduce the stimulation and harm to seahorses as much as possible. Seahorses may be under reproductive disturbance or abortion if they were stimulated at this moment, and epidermal injury may easily cause infection of pathogenic bacterium on seahorses which will enhance the risk of disease.

After parents were put into the white buckets, stimulation of slight water flow in 0.05 m³/h was maintained. Seahorses mostly mate at morning, and a quiet environment is provided so as to prevent the generation of disturbances to the seahorses.

3. Rearing and nursing of pregnant seahorses and collection of postlarvae

After staying in the white bucket for 2~7 days, male and female parents were first in heat, moved in parallel and chased each other, when reaching climax, the brood pouch of the male began to bulge and a pouch opening mouth opened, while genital of the female extruded. When tails of male and female twined together, ovum was ovulated by the female into the brood pouch of the male, and the fertilization was completed. During pregnancy, male seahorses are weak and sensitive to external disturbance, so they need fine nursing. Thus, the environment of aquaculture should be kept quiet and temperature difference of water was maintained to no more than 3° C.; operation should be fast and gentle during artificial inspection on physical condition of the seahorses, also seahorses should not be kept out of water for more than 2 minutes. Daily feeding amount during pregnancy should be reduced compared to the period without pregnancy, and seahorses were fed with frozen shrimps 4~5 times daily while the total feeding amount was 4%~7% of the weight of seahorse. The male discharged the fertilized eggs after which grew in the brood pouch for 15~22 days.

Time of fertilization and pregnancy of seahorses vary, thus, time of spawn of parents varies too. In order to avoid errors made by the difference in time of birth, postlarvae newly hatched from Apr. 4, 2013 to Apr. 11, 2013 were collected in this experiment (all postlarvae hatched by each breeding group in one week were only collected respectively).

4. Rearing of postlarvae in same management way and similar conditions.

Reproductive filial generations of seahorse from each group were put into buckets (the volume is 1 m³) separately for rearing, and density was 500 seahorses/m³. During this time, feeding amount of baits was properly increased daily. Seahorses were fed with artemia nauplii as bait mainly and the suitable feeding amount of baits is whereby a little bit of the baits are left in water when the seahorses were fed again.

Along with the growth of individuals, when they were 1 month old, 900 seahorse larvae were selected randomly from each breeding group and transferred to a small size concrete pond (the volume is 9 m³) for rearing, and density was 100 seahorses/m³. Lined seahorses were fed with artemia nauplii and frozen shrimps while daily feeding amount of frozen shrimps was 5%~8% of total weight of seahorses.

When they were 2 months old, lined seahorses were transferred to an adult fish rearing pond (the volume is 16 m³) for raising and rearing, and density was 20 seahorses/m³. Until lined seahorses were 4 months old, they were fed with frozen shrimps during this period while daily feeding amount of frozen shrimps was 5%~8% of total weight of seahorses.

5. Comparison of survival rate and growth performance of the filial generations (1) On May 6~May 8, June 8~June 9 and Aug. 7~Aug. 9, 2013, survival rate of each breeding group was calculated respectively.

By calculation and analysis, we discovered that the survival rate of purebred lined seahorse at 4 months old was 68.64%~72.67%, the average was 70.58%; the survival rate of hybrid lined seahorse was 71.38%~79.60%, the average was 75.29%, which increased by 6.70% as compared to the purebred.

Wherein, heterosis of Dongshan♀×Shenzhen♂ was the most obvious, which increased by 11.26% of the purebred; those groups of which heterosis was over 8% were Dongshan♀×Yantai♂, Yantai♀×Dongshan♂ and Shenzhen♀×Yantai♂ (as shown in Table 1 and FIG. 1).

TABLE 1

Survival rates of F1 generations of lined seahorse at 1, 2, and 4 months old

| Group | | 1 Month old (%) | 2 Months old (%) | 4 Months old (%) | Heterosis at 4 months old (%) |
|---|---|---|---|---|---|
| Purebred | Yantai♀ × Yantai♂ | 80.34 | 72.22 | 68.64 | — |
| | Shenzhen♀ × Shenzhen♂ | 84.65 | 77.56 | 72.67 | — |
| | Dongshan♀ × Dongshan♂ | 83.78 | 75.42 | 70.42 | — |
| | Avg. of the purebred | 82.92 | 75.07 | 70.58 | — |

TABLE 1-continued

Survival rates of F1 generations of lined seahorse at 1, 2, and 4 months old

| | Group | 1 Month old (%) | 2 Months old (%) | 4 Months old (%) | Heterosis at 4 months old (%) |
|---|---|---|---|---|---|
| Hybrid | Yantai♀ × Shenzhen♂ | 82.75 | 75.55 | 73.33 | 3.79 |
| | Yantai♀ × Dongshan♂ | 84.36 | 78.64 | 75.56 | 8.67 |
| | Shenzhen♀ × Yantai♂ | 87.57 | 78.25 | 76.67 | 8.51 |
| | Shenzhen♀ × Dongshan♂ | 86.87 | 74.78 | 71.38 | −0.23 |
| | Dongshan♀ × Yantai♂ | 85.70 | 77.32 | 75.22 | 8.18 |
| | Dongshan♀ × Shenzhen♂ | 88.22 | 80.14 | 79.60 | 11.26 |
| | Avg. of the hybrid | 85.91 | 77.45 | 75.29 | 6.70 |

(2) On Aug. 7~9, 2013, 100 seahorses were randomly selected from each rearing pond and weighed.

By calculation and analysis, we discovered that the average weight of purebred lined seahorse at 4 months old was 5.20~5.35 g, the average was 5.27 g; the weight of hybrid lined seahorse was 5.37~5.76 g, the average was 5.61 g, which increased by 6.32% as compared to the purebred.

Figure 2:
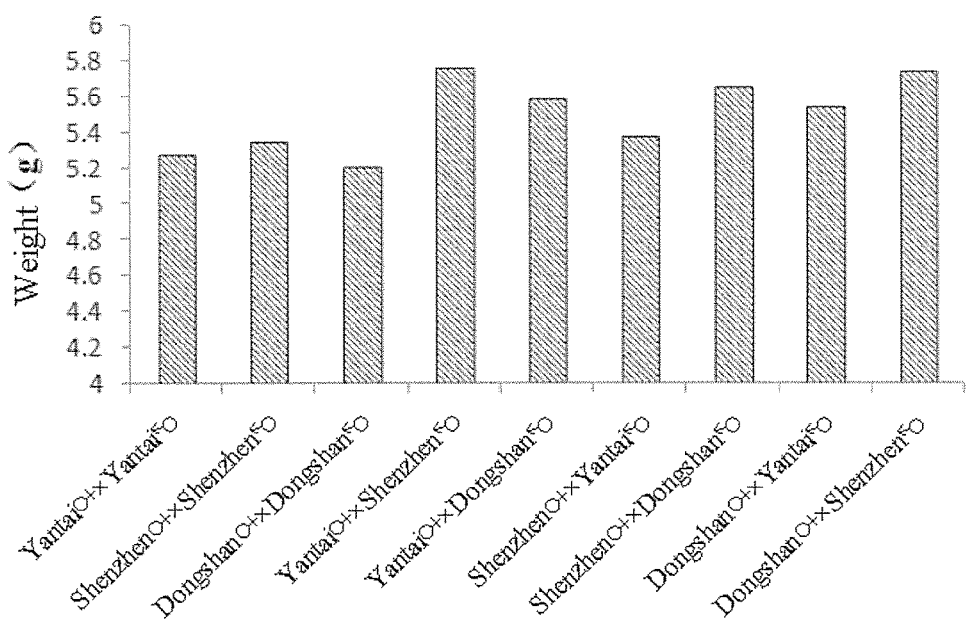
FIG. 2 shows the schematic drawing of weight of diallel cross filial generations from lined seahorse populations of Shenzhen, Dongshan and Shandong.

Wherein, average weights of Yantai♀×Shenzhen♂, Dongshan♀×Shenzhen♂ and Shenzhen♀×Dongshan♂ were the highest, being 5.76 g, 5.74 g and 5.65 g respectively; heterosis of groups Dongshan♀×Shenzhen♂, Yantai♀×Dongshan♂ and Yantai♀×Shenzhen♂, was the most obvious, being 8.81%, 8.47% and 7.11% respectively (as shown in Table 2 and FIG. 2).

TABLE 2

Weights of F1 generations of lined seahorse at 4 months old

| | Group | Avg. of weight (g) | Standard deviation (g) | Minimum (g) | Maximum (g) | Heterosis of the hybrid at 4 months old (%) |
|---|---|---|---|---|---|---|
| Purebred | Yantai♀×Yantai♂ | 5.27 | 1.38 | 3.58 | 6.54 | — |
| | Shenzhen♀×Shenzhen♂ | 5.35 | 1.49 | 3.46 | 6.68 | — |
| | Dongshan♀×Dongshan♂ | 5.20 | 1.26 | 3.43 | 6.65 | — |
| | Avg. of the purebred | 5.27 | | | | — |
| Hybrid | Yantai♀×Shenzhen♂ | 5.76 | 1.78 | 3.44 | 6.75 | 8.47 |
| | Yantai♀×Dongshan♂ | 5.58 | 1.56 | 3.58 | 6.94 | 6.59 |
| | Shenzhen♀×Yantai♂ | 5.37 | 1.25 | 3.61 | 6.68 | 1.13 |
| | Shenzhen♀×Dongshan♂ | 5.65 | 1.29 | 3.38 | 6.87 | 7.11 |
| | Dongshan♀×Yantai♂ | 5.54 | 1.46 | 3.59 | 6.98 | 5.82 |
| | Dongshan♀×Shenzhen♂ | 5.74 | 1.70 | 3.57 | 7.04 | 8.81 |
| | Avg. of the hybrid | 5.61 | | | | 6.32 |

Thus, survival rate and growth rate of the filial generation in the present invention obtained by hybridization of different geographical populations, increased apparently compared to those filial generations without hybridization; simultaneously genetic diversity level of the filial generation was increased due to the great difference in genetic background of parents, which is beneficial for the subsequent breeding of fine species of lined seahorse.

Embodiment 2 Influence of Parents Selecting on Breeding for Heterosis

By abundant exploratory developments and verifications in the present invention, in the procedure of breeding method for heterosis, from selecting parents, breeding parents, control of hybridization condition, fine nursing of pregnant seahorse, to acquisition of filial generations with heterosis in the end, operation and control of condition for each link exhibit interesting relations with survival rate and growth situation of filial generation with heterosis, and have important impact on the result of crossbreeding.

Controlling of several objective conditions was taken as example in the present embodiment to illustrate the pivotal role for each link in such breeding method.

1. Experiment Grouping (1) Experimental group: breeding and propagation according to following breeding method for obtaining heterosis in lined seahorses:

S1, the same as embodiment 1, lined seahorses which were energetic, disease-free, harmless, healthy and strong, with well-developed gonad, were selected as parents from aquaculture populations of Shenzhen Guangdong and Yantai Shandong. Ages of the parents were 1~1.5 years old, weights of male seahorse parents were no less than 10.0 g, weights of female seahorse parents were no less than 8.0 g, and differences of weights between male parents or female parents was no more than 2.0 g.

S2, intensified rearing of lined seahorse parents in S1: in 1~2 month after seahorse parents were introduced, they were separated from each other to be raised and bred alone for half month. During rearing of parents, water temperature was maintained between 22~30° C. The parents were fed with frozen shrimps mainly accompanied by copepods and artemia nauplii as baits for intensified rearing. Daily feeding amount of frozen shrimps was 5%~8% of total weight of lined seahorses and there were three feedings every day which were at 8 a.m., 1 p.m. and 6 p.m. respectively.

S3, matching seahorses according to group Yantai♀ × Shenzhen♂: parents were put into imitating ecotype white buckets for matching and breeding. After parents were put into the white buckets, stimulation of slight water flow in 0.05 m³/h was maintained. A quiet environment was guaranteed on every morning. Wherein, each imitating ecotype white bucket contained 4 pairs or more than 4 pairs of parents and each breeding group comprised 12 pairs or more than 12 pairs of parents. Each imitating ecotype white bucket contained same amount of female and male parents respectively. During operation, make sure the seahorses are handled gently and put latex gloves on. Seahorses twining together were separated gently under water in order to reduce the stimulation and harm to seahorses as much as possible.

S4, pregnant parents obtained from S3 were under fine nursing to avoid abortion; specific conditions are as follows: a quiet environment of aquaculture was maintained and temperature difference of water was no more than 3° C.; operation should be fast and gentle during artificial inspection on physical condition of the seahorse, also the seahorses should not be kept out of water for more than 2 minutes; daily feeding amount during pregnancy should be reduced compared to the period without pregnancy, and seahorses were fed with frozen shrimps 3~5 times daily while the total feeding amount was 4%~7% of the weight of seahorse.

S5, all filial generations hatched by pregnant parents in S4 in one week were collected respectively;

S6, the filial generations in S5 were put into the buckets separately for rearing in similar environment and in same feeding mode, and density was 500 seahorses/m³. Seahorses were fed with artemia nauplii as baits mainly, and the suitable feeding amount of baits is whereby a little bit of the baits are left in water when seahorses were fed again. When lined seahorses were 1 month old, they were transferred to a small size concrete pond for rearing, and density was 100 seahorses/m³. Lined seahorses were fed with artemia nauplii and frozen shrimps while daily feeding amount of frozen shrimps was 5%~8% of total weight of seahorses. When lined seahorses were 2~3 months old, they were transferred to an adult fish rearing pond for rearing, and density was 20 seahorses/m³. Lined seahorses were fed with frozen shrimps while daily feeding amount of frozen shrimps was 5%~8% of total weight of seahorses.

S7, the survival rates of filial generations were compared when lined seahorses were 1, 2 and 4 months old respectively. When lined seahorses were 4 months old, weights of lined seahorses were compared. Fine strain of lined seahorse with high survival rate, fast growth rate and good genetic diversity was obtained.

(2) Control group 1: breeding and propagation method was same with the experimental group; the difference was that ages of parents selected in S1 were 6~7 months old.

(3) Control group 2: breeding and propagation method was same with the experimental group; the difference was that weights of male parents selected in S1 were 6.0~8.0 g and weights of female parents selected in S1 were 4.0~6.0 g.

(4) Control group 3: breeding and propagation method was same with the experimental group; the difference was that ages of parents selected in S1 were more than 3 years old.

2. Experimental Results

By comparison of survival rates of filial generations at 1, 2, and 4 months old and comparison of weights of lined seahorse from each group at 4 months old, the experimental group obtained the highest survival rate and fastest growth rate. Specific data are shown in Table 3 and Table 4.

TABLE 3

Survival rates of F1 generations of lined seahorse from each group at 1, 2, and 4 months old

| Group | 1 month old (%) | 2 months old (%) | 4 months old (%) |
|---|---|---|---|
| Experimental group | 82.75 | 75.55 | 73.33 |
| Control group 1 | 64.21 | 60.14 | 58.65 |
| Control group 2 | 69.32 | 65.46 | 63.18 |
| Control group 3 | 70.41 | 67.38 | 64.14 |

It can be seen from the data in Table 3 that, survival rates of the experimental group are all much higher than that of each control group. It indicates that in the crossbreeding system in the present invention, standards of age and weight of seahorse parents have obvious influence on survival rates of the filial generations.

TABLE 4

Weights of F1 generations of lined seahorse at 4 months old

| Group | Avg. weight (g) | Minimum (g) | Maximum (g) |
|---|---|---|---|
| Experimental group | 5.76 | 3.44 | 6.75 |
| Control group 1 | 5.12 | 2.51 | 5.94 |
| Control group 2 | 5.25 | 2.32 | 5.85 |
| Control group 3 | 5.45 | 3.41 | 6.55 |

It can be seen from the data in Table 4 that, average weight of the experimental group is 5.76 g, which is much higher than that of each control group. It indicates that in the crossbreeding system in the present invention, standards of age and weight of seahorse parent have obvious influence on growth rates of the filial generations.

Apparently, above-mentioned embodiments are merely for clarity of the description, but do not limit the forms of embodiment in present invention. To ordinary skilled in the art, other different forms of transformation or variation can be performed based on the above-mentioned description and idea, and thus, it's not necessary and unable for all forms of embodiment to be exhaustive. It is therefore to be understood that any modifications, equivalent replacements and improvements that are devised within the spirit and scope and principle of the present invention should be included in the scope of protection as defined by the appended claims of the present invention.

What is claimed:

1. A breeding method for obtaining heterosis in lined seahorses, comprising the following steps:
    S1, selecting parents of lined seahorse from populations with differences in genetic background;
    S2, intensified rearing the parents of lined seahorse in S1;
    S3, completely diallel crossing, matching and breeding the parents of lined seahorse from different populations in S2 according to provenance and classifying into a plurality of different breeding groups;
    S4, finely nursing pregnant parents of each of the different breeding groups obtained in S3 to avoid abortion;
    S5, respectively collecting all filial generations hatched by the pregnant parents of each of the different breeding groups in S4 in one week;
    S6, finely nursing the filial generations of the different breeding groups in S5 according to a feeding mode in an environment;
    S7, comparing survival rate and growth performance of the filial generations of the different breeding groups in S6 to obtain a strain of the lined seahorses with high survival rate, fast growth rate and good genetic diversity among the different breeding groups.

2. The breeding method according to claim 1, wherein aquaculture populations of Shenzhen Guangdong, Dongshan Fujian and Yantai Shandong are selected as the parents in S1; ages of parents are 1~1.5 years old, weights of male parents are over 10.0 g and weights of female parents are over 8.0 g.

3. The breeding method according to claim 1, wherein the lined seahorses which are energetic, disease-free, healthy and strong, with well-developed gonad, are selected as the parents in S1, and differences of weights between all male parents or female parents are less than or equal to 2.0 g.

4. The breeding method according to claim 1, wherein specific methods for the intensified rearing described in S2 are as follows: in 1~2 months after the parents of lined seahorse have been introduced, male and female parents are separated for feeding and are reared alone for half month; during this period, water temperature is maintained between 22~30° C.; the parents are under intensified rearing by being fed with frozen shrimps mainly accompanied by copepods as well as artemia nauplii as baits; daily feeding amount of frozen shrimps is 5%~8% of total weight of the lined seahorses; and there are three feedings every day which are at 8 a.m., 1 p.m. and 6 p.m. respectively.

5. The breeding method according to claim 1, wherein specific methods for the complete diallel cross of parents according to the provenance described in S3 are as follows:

S31, performing matching in accordance with nine breeding groups: Yantai♀×Yantai♂, Yantai♀×Shenzhen♂, Yantai♀×Dongshan♂, Shenzhen♀×Shenzhen♂, Shenzhen♀×Yantai♂, Shenzhen♀×Dongshan♂, Dongshan♀×Dongshan♂, Dongshan♀×Yantai♂ and Dongshan♀×Shenzhen♂;

S32, respectively putting the parents of each breeding group in S31 into imitating ecotype white buckets for matching and breeding; each of the imitating ecotype white bucket contains 4 pairs or more than 4 pairs of parents; each breeding group comprises 12 pairs or more than 12 pairs of parents.

6. The breeding method according to claim 5, wherein each of the imitating ecotype white bucket described in S32 contains same amount of female and male parents respectively; during operation, make sure the seahorses are handled gently and put latex gloves on; the seahorses twining together are separated gently under water in order to reduce the stimulation and harm to the seahorses as much as possible.

7. The breeding method according to claim 6, wherein after the parents are put into the imitating ecotype white buckets, stimulation of slight water flow in 0.05 m³/h is maintained.

8. The breeding method according to claim 1, wherein specific methods for the finely nursing described in S4 are as follows: temperature difference of water is no more than 3° C.; an inspection on the physical condition of the seahorse being performed out of water is no more than two minutes; daily feeding amount during pregnancy should be reduced compared to the period without pregnancy, and the seahorses are fed with frozen shrimps 3~5 times daily while the total feeding amount is 4%~7% of the weight of the seahorse.

9. The breeding method according to claim 1, wherein conditions and management ways of the filial generations of the different breeding groups finely nursing in S6 are substantially the same to each other, wherein the filial generations of the different breeding groups are put into buckets separately for rearing, with density being 500 seahorses/m³, and the seahorses are fed with artemia naupliis as baits mainly, and the suitable feeding amount of baits is whereby a little bit of the baits are left in water when the seahorses are fed again; when the lined seahorses are 1 month old, they are transferred to a small size concrete pond for rearing, with density being 100 seahorses/m³, and the lined seahorses are fed with artemia nauplii and frozen shrimps while daily feeding amount of frozen shrimps is 5%~8% of total weight of the seahorses; when the lined seahorses are 2~3 months old, they are transferred to an adult fish rearing pond for rearing, with density being 20 seahorses/m³, and the lined seahorses are fed with frozen shrimps while daily feeding amount of frozen shrimps is 5%~8% of total weight of the seahorses.

10. The breeding method according to claim 1, wherein specific methods for the comparison of survival rate and growth performance of the filial generations described in S7 are as follows: the survival rates of the filial generations from each breeding group are compared when the lined seahorses are 1, 2 and 4 months old respectively; when the lined seahorses are 4 months old, weights of the lined seahorses from each breeding group are compared.

* * * * *